(12) United States Patent
Mateu et al.

(10) Patent No.: US 9,023,324 B2
(45) Date of Patent: May 5, 2015

(54) COSMETIC COMPOSITION FOR SKIN CARE

(75) Inventors: Juan R. Mateu, Oak Ridge, NJ (US);
Domnica Cernasov, Ringwood, NJ (US); Craig Arpino, Ramsey, NJ (US); Ralph Macchio, Sparta, NJ (US); Irina Staina, Bethlehem, PA (US)

(73) Assignee: Coty Deutschland GmbH, Mainz (DE)

( * ) Notice: Subject to any disclaimer, the term of this patent is extended or adjusted under 35 U.S.C. 154(b) by 1394 days.

(21) Appl. No.: 11/997,645

(22) PCT Filed: Jul. 28, 2006

(86) PCT No.: PCT/EP2006/064773
§ 371 (c)(1),
(2), (4) Date: Jun. 11, 2008

(87) PCT Pub. No.: WO2007/014908
PCT Pub. Date: Feb. 8, 2007

(65) Prior Publication Data
US 2008/0317686 A1    Dec. 25, 2008

Related U.S. Application Data

(60) Provisional application No. 60/706,487, filed on Aug. 8, 2005.

(30) Foreign Application Priority Data

Aug. 3, 2005   (DE) .......................... 10 2005 037 800

(51) Int. Cl.
| | | |
|---|---|---|
| A61K 8/89 | (2006.01) | |
| A61K 8/06 | (2006.01) | |
| A61Q 1/04 | (2006.01) | |
| A61Q 1/06 | (2006.01) | |
| A61Q 1/08 | (2006.01) | |
| A61Q 1/10 | (2006.01) | |
| A61Q 15/00 | (2006.01) | |
| A61Q 17/04 | (2006.01) | |
| A61Q 19/00 | (2006.01) | |
| A61K 8/02 | (2006.01) | |
| A61K 8/898 | (2006.01) | |
| A61Q 1/02 | (2006.01) | |
| A61Q 17/00 | (2006.01) | |
| A61Q 19/10 | (2006.01) | |

(52) U.S. Cl.
CPC ................. *A61K 8/06* (2013.01); *A61K 8/0212* (2013.01); *A61K 8/898* (2013.01); *A61Q 1/02* (2013.01); *A61Q 1/06* (2013.01); *A61Q 1/10* (2013.01); *A61Q 15/00* (2013.01); *A61Q 17/00* (2013.01); *A61Q 19/00* (2013.01); *A61Q 19/10* (2013.01); *A61Q 1/04* (2013.01)

(58) Field of Classification Search
USPC ...................... 424/59, 78.03, 65, 64, 70.7, 63
See application file for complete search history.

(56) References Cited

U.S. PATENT DOCUMENTS

| | | | |
|---|---|---|---|
| 5,645,822 A * | 7/1997 | Meyer et al. .................... | 424/59 |
| 2002/0035070 A1* | 3/2002 | Gardlik et al. .................. | 514/23 |
| 2004/0170590 A1 | 9/2004 | Fahnestock et al. | |
| 2005/0019285 A1* | 1/2005 | Lee et al. ........................ | 424/63 |
| 2005/0089486 A1* | 4/2005 | Spindler et al. ................. | 424/59 |

FOREIGN PATENT DOCUMENTS

| | | | |
|---|---|---|---|
| DE | 101 44 235 A1 | 3/2003 | |
| WO | WO 03/022235 A2 * | 3/2003 | ............... A61K 7/48 |

OTHER PUBLICATIONS

Trimethylsilylamodimethicone: retrieved from internet: http://www.specialchem4cosmetics.com/services/inci/ingredient.aspx?id=14248. Retrieved on Dec. 9, 2013.*
DC 2-8566 MSDS: retrieved from internet: http://www.dowcorning.com/applications/search/?R=1250EN. Retrieved on Dec. 9, 2013.*
DC 2-8566 Scifinder: retirved from internet: https://scifinder.cas.org/scifinder/view/scifinder/scifinderExplore.jsf. retrieved on Dec. 9, 2013.*

* cited by examiner

*Primary Examiner* — Ernst V Arnold
*Assistant Examiner* — Hong Yu
(74) *Attorney, Agent, or Firm* — Novak Druce Connolly Bove + Quigg LLP

(57) ABSTRACT

The invention relates to the use of siloxanes for emulsifiers for cosmetic compositions for skin care as well as cosmetic emulsions comprising such emulsifiers. The composition comprises an aminofunctional organopolysiloxane for W/O emulsions, O/W emulsions and multiple emulsions. The emulsions are formed easily, are very stable and needs not to add electrolytes.

15 Claims, No Drawings

COSMETIC COMPOSITION FOR SKIN CARE

CROSS REFERENCE TO RELATED APPLICATIONS

This application is a National Stage Entry of PCT/EP2006/064773, filed Jul. 28, 2006, which claims priority to U.S. Provisional Application No. 60/706,487, filed Aug. 8, 2005, and to DE 10 2005 037 800.5, filed on Aug. 3, 2005, the entireties of which are incorporated herein by reference.

FIELD OF THE INVENTION

The invention relates to the use of siloxanes for emulsifiers for cosmetic skin care compositions as well as cosmetic skin care compositions comprising such emulsifiers.

PRIOR ART

From the state of the art it is known that aminofunctional siloxanes are active ingredients for hair conditioning by enhancing wet and dry combability and reducing triboelectric charging. Also haircolouring formulations and permanent waving products comprise such siloxanes. E.g. U.S. Pat. No. 5,804,173 refers to personal care compositions and shows in example 13 a hair styling rinse composition which comprises in premix A Amodimethicone as a known hair conditioner.

SUMMARY OF THE INVENTION

Object of the invention is the development of cosmetic compositions for skin care with a new emulsifying agent.

A further object is the preparation of skin care compositions using an organopolysiloxan as emulsifier.

The cosmetic composition for skin care of the invention comprises as emulsifying agent in cosmetic O/W emulsions, W/O emulsions or multiple emulsions 0.1 to 10% by weight of an aminofunctional organopolysiloxane.

It has been found that the use of certain amino functional organopolysiloxanes leads very quickly to stable emulsions without any further emulsifier.

The aminofunctional organopolysiloxane comprises in a preferred embodiment 3-(2-aminoethyl)-aminopropyl groups.

The aminofunctional organopolysiloxane has an amine equivalent of 1800 to 4500 g/mol, preferably an amine equivalent of 1800 to 2200 g/mol.

The aminofunctional organopolysiloxane is e.g. comprised as a main substance in the cosmetic product with the INCI name Amodimethicone. Suppliers of that product are e.g. Wacker-Chemie GmbH, Deutschland Wacker-Belsil® ADM 6057E; Dow Corning Corp., Midland, USA, DC 2-8566 Amino Fluid; GE Silicones, Waterford, USA, SM2658®. A further preferred product is KF-880® or KF-8704® of Shin-Etsu.

The cosmetic skin care composition of the invention comprises O/W emulsions, W/O emulsions or multiple emulsions or micro emulsions. Multiple emulsions are e.g. W/O/W emulsions, O/W/O emulsions, Si/W/O emulsions etc.

The term "skin care composition" refers to usual creams, lotions or sticks as well as products of decorative cosmetic such as lipsticks, mascara etc. with the proviso that hair conditioning products or hair colouring products are excepted.

The emulsions formed using the new emulsifier instead of typical emulsifiers used in the industry are as good and in most cases better than conventionally made emulsions. The emulsions are formed very quickly and easily at high or low temperatures usually without the use of a homogenizator. The amount of emulsifier needed for a 30-50% by weight aqueous phase ranges from 0.5 to 2%. The stability of emulsions with the new aminofunctional emulsifier surpasses conventional emulsions.

If e.g. the new skin care composition is present as a stick they can comprise up to 55% by weight water, preferably 40-55% by weight and specifically 48-55% by weight. Such sticks comprise also antiperspirant sticks and deodorant sticks. The sticks do not show any sweat out processes at such high contents of water.

Specifically to underline is that with such small concentrations of the emulsifying agent of 0.5 to 0.6% by weight it is possible to emulsify up to 50% by weight water without problems. W/O emulsions, O/W emsulsions, Si/W emulsions or W/Si emulsions or other con be prepared equally good.

Further it is possible to include high shares of pigments as usual for decorative cosmetics because of the easily wettability. Also color platelets are to include in silicone emulsions with the instant emulsifying agent.

It is common practice to add electrolytes to conventional emulsions to create stable emulsions. The new emulsion can be made without electrolytes and pass all stability criteria common to the cosmetic industry. It also has the added benefit of reducing surface tension in the emulsion, therefore, no anti-foam agents are required.

The inventive emulsions for skin care comprises also cosmetic auxiliary and carrier substances as they are used conventionally in such compositions, for example, preservatives, colorings, pigments with coloring effect, thickeners, fragrances, alcohols, polyols, esters of polyols, polar and nonpolar oils, polymers, copolymers, additional emulsifiers, waxes, stabilizers etc.

Additional cosmetic active agents which can be used include e.g. inorganic and organic sunscreens, scavengers, moisturizing substances, vitamins, enzymes, vegetable active agents, polymers, copolymers, melanin, antioxidants, anti-inflammatory natural active agents, fluorosilicones etc.

For the invention used oils can be usual cosmetic oils such as mineral oil, hydrogenated polyisobutene, squalane from synthetic or natural sources, cosmetic esters or ethers, which can be branched or unbranched, saturated or unsaturated, vegetable oils, fluorinated oils or mixtures of two or more thereof.

Especially suitable oils are, for example, silicone oils, fluorinated oils, mineral oils, hydrogenated polyisobutene, polyisoprene, squalane, tridecyltrimellitate, trimethylpropane truisostearate, isodecylcitrate, neopentyl glycol diheptanoate, PPG-15-stearyl ether, Calendula oil, Jojoba oil, Avocado oil, Macadamia nut oil, Castor oil, Cocoa butter, Coconut oil, Corn oil, Cotton seed oil, Olive oil, Palm kernel oil, Rapeseed oil, Safflower seed oil, Sesame seed oil, Soybean oil, Sunflower seed oil, Wheat germ oil, Grape kernel oil, Kukui nut oil, Thistle oil, and mixtures thereof.

Preferred are also mixtures of volatile silicone oils with high molecular polydimethyl siloxanes, e.g. Cyclomethicone or Dimethicone and Dimethiconol. Such mixtures have a viscosity in the range of 400-6000 mPa·s at a relation of the volatile silicons to the high molecular silicones in the range of 6-15:1. Liquid waxes can be present in shares of 1-80% by weight, solid waxes up to about 15% by weight.

They show a special shiny film and a silky smooth film also without water in the formula.

Special preferred are monoesters, diesters, triesters, hydrocarbons, volatile and non-volatile alkanes and alkenes.

Preferred alkanes are isododecane, isohexadecane or mixtures thereof. Preferred alkenes are (INCI name): Hydrogenated or Unhydrogenated Polyisobutene, Polyisoprene, Polystyrene, Polybutylene, Polyethylene, Polybutadienes.

Suitable esters of polyols are esters of $C_{10}$-$C_{15}$ fatty acids and alcohols, esters of $C_{10}$-$C_{15}$ fatty acids and glycols, or esters of hydroxy fatty acids. Branched $C_{12}$-$C_{15}$ alkyl esters in conjunction with other esters such as di- or tri-esters of polyols are particularly advantageous in the oil phase, with esters of linear-chain alcohols and branched acids being particularly favourable. All these suitable esters are derived from primary alcohols.

Suitable substances for the oil phase include Neopentyl Glycol Diheptanoate, Propylene Glycol Dicaprylate, Dioctyl Adipate, Diisopropyl Dimer Dilinoleate, Diisostearyl Dimer Dilinoleate, $C_{12-13}$ Alkyl Lactate, Di-$C_{12-13}$ Alkyl Tartrate, Tri-$C_{12-13}$ Alkyl Citrate, $C_{12-15}$ Alkyl Lactate, PPG Dioctanoate, Diethylene Glycol Dioctanoate, meadowfoam oil, babassu oil, jojoba oil, rice oil, $C_{12-15}$ Alkyl Oleate, avocado oil, Tridecyl Neopentanoate, beeswax, Cetearyl Alcohol and Polysorbate 60, candelilla wax, $C_{18-26}$ Triglycerides, Cetearyl Alcohol & Cetearyl Glucoside, acetylated lanolin, Glyceryl Hydroxystearate, $C_{18-36}$ Acid Glycol Ester, with substances such as $C_{18-36}$ triglycerides, Glyceryl Hydroxystearate, candelilla wax, and mixtures thereof being particularly favourable.

Polyols, which are also possible ingredients of the emulsions of the invention, are e.g. propylene glycol, dipropylene glycol, ethylene glycol, isoprene glycol, glycerin, butylene glycols, sorbitol and mixtures thereof.

Waxes for preparation of inventive emulsions may be selected among natural plant waxes, animal waxes, natural and synthetic mineral waxes and synthetic waxes. There are included carnauba wax, candelilla wax, ozokerite, beeswax, montan wax, wool wax, ceresiner micro-waxes, paraffin waxes, petrolatum, silicon wax, polyethylene glycol waxes or polyethylene glycolester waxes. Preferred waxes are carnauba wax, candelilla wax, castor wax, olive wax, beeswax, micorocrystalline wax, ozokerite, polyethylene wax. Waxes can be present in shares up to 20% by weight.

The use of film-forming agents in the inventive emulsions is also possible. Film-forming agents are acrylates, polyurethanes, PVP and PVP copolymers. A preferred film-forming agent is Sucrose Acetate Isobutyrate. Other preferred film forming agents would be alkenes such as high molecular weight polybutenes e.g. Polybutene (INCI).

The use of thickeners and hydrocolloids in the inventive emulsions is also possible. Thickeners are bentone, thixcin, electrolytes such as sodium chloride, metal soaps etc.

The emulsions according to the invention can also advantageously contain antioxidants. Antioxidants include vitamins such as vitamin C and derivatives thereof, for example, ascorbic acetate, phosphate, and palmitate; vitamin A and derivatives thereof; folic acid and derivatives thereof, vitamin E and derivatives thereof, such as tocopheryl acetate; flavones or flavonoids; amino acids, such as histidine, glycine, tyrosine, tryptophan, and derivatives thereof; imidazole such as cis- or trans-urocaninic acid and their derivatives; peptides such as D,L-carnosine, D-carnosine, L-carnosine and their derivatives carotenoids and carotenes such as, for example, α-carotene, β-carotene; lycopine; uric acid and derivatives thereof; α-hydroxy acids such as citric acid, lactic acid, malic acid; α-hydroxy fatty acids such as palmitic acid, phytic acid, lactoferrin; stilbenes and their derivatives; mannose and their derivatives; liponic acid and their derivatives such as dihydro liponic acid; ferula acid and their derivatives; thiols such as glutathione, cysteine and cystine.

The addition of vitamin A or vitamin A palmitate (retinol) and vitamin E is especially preferred.

It is moreover advantageous to add to the emulsions according to the invention corresponding water and/or oil soluble UVA or UVB filters or both. Advantageous oil-soluble UVB filters include 4-amino benzoic acid derivatives such as 4-(dimethylamino)-benzoic acid-(2-ethylhexyl) ester; esters of cinnamic acid such as 4-methoxy cinnamic acid (2-ethylhexyl) ester, benzophenone derivatives such as 2-hydroxy-4-methoxy benzophenone; 3-benzylidene camphor derivatives such as 3-benzylidene camphor.

Preferred oil-soluble UV filters are Benzophenone-3, Butyl-Methoxybenzoylmethane, Octyl Methoxycinnamate, Octyl Salicylate, 4-Methylbenzylidene Camphor, Homosalate and Octyl Dimethyl PABA.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters include dibenzoyl methane derivatives such as 1-phenyl-4-(4'-isopropanolphenyl) propane1,3-dione.

Special preferred are Benzophenone-3, Butyl Methoxy-dibenzoylmethane, Octyl Methoxycinnamate, Octyl Salicylate, 4-Methylbenzylidene Camphor, Homosalate, Octocrylene, Ethylhexyl Methoxycinnamate, Isoamyl-p-Methoxycinnamate, Octyl Dimethyl PABA, Ethylhexyltriazone, Diethylhexyl Butamido Triazone, Ethylhexyl Salicylate, Methylene Bis-Benzotriazolyl Tetramethylbutylphenol, Disodium Phenyl Dibenzimidazole Tetrasulfonate, Bis-Ethylhexyloxyphenol Methoxyphenyl Triazine.

Preferred as sunscreen filters are inorganic pigments on the basis of metal oxides, such as $TiO_2$, $SiO_2$, ZnO, $Fe_2O_3$, $ZrO_2$, MnO, $Al_2O_3$, which can also be used in mixtures thereof.

Especially preferred as inorganic pigments are agglomerate substrates of $TiO_2$ and/or ZnO according to WO99/06012 which have a contents of spherical and porous $SiO_2$ particles, wherein the $SiO_2$ particles have a particle size in the range of 0.05 μm to 1.5 μm, and, in addition to the $SiO_2$ particles, other inorganic particle-like substances with spherical structure are present, wherein the spherical $SiO_2$ particles form defined agglomerates with the other inorganic substances with a particle size in the range of 0.06 μm to 5 μm.

In the inventive emulsions are also usable humectants such as glycerine, butylene glycol, propylene glycol and mixtures thereof.

When the emulsions of the present invention contains additionally softeners, the softeners can be normally provided in the form of a plurality of compounds, such as stearyl alcohol, glyceryl mono ricinoleate, glyceryl mono stearate, propane-1,2-diol, butane-1,3-diol, cetyl alcohol, isopropyl isostearate, stearic acid, isobutyl palmitate, oleyl alcohol, isopropyl laurate, decyl oleate, octadecane-2-ol, isocetyl alcohol, cetyl palmitate, silicone oils such as dimethylpolysiloxane, isopropyl myristate, isopropyl palmitate, polyethylene glycol, lanolin, cocoa butter, vegetable oils such as corn oil, cotton seed oil, olive oil, mineral oils, butyl myristate, palmitic acid etc.

Pigments, pigment mixtures or powders with a pigment-like effect, also including those with a pearl-gloss effect, may include, for example, iron oxides, aluminum silicates such as ochre, titanium oxide, mica, kaolin, manganese containing clays such as umber and red bole, calcium carbonate, French chalk, mica-titanium oxide, mica-titanium oxide-iron oxide, bismuth oxychloride, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye. Also other fillers such as talc, PMMA, polyurethane are usable in the inventive emulsions.

Also usual colorants, treated and untreated dyes can be used.

Within the inventive emulsion the share of pigments such as nylon beads can be up to about 30% by weight, other pigments can be present up to 20% by weight.

The addition of electrolytes causes the solubility behaviour of an additionalls added hydrophilic emulsifier to change, but the addition of electrolytes is not preferred. Hydrophilic emulsifiers are subject to a partial phase inversion during which the oil phase solubilizes water. The result is a stable emulsion, in particular a micro-emulsion or an O/W/O-emulsion. Suitable electrolytes are salts containing the following anions: chlorides, inorganic oxo-element anions, such as borates, aluminates, sulphates, phosphates, carbonates. Electrolytes based on organic anions include citrates, tartrates, lactates, propionates, acetates and benzoates as well as EDTA and salts thereof.

Cations of the salts can be alkali metal ions, alkaline earth metal ions, ammonium ions, alkyl ammonium ions, iron ions, zinc ions.

Additional electrolytes, if any, can be contained in the range of 0.01 to 3% by weight, preferably 0.1 to 2.5% by weight.

The use of the cosmetic skin care composition according to the invention, for example, can be realized in the form of sun screen creams, after sun products, day creams, night creams, masques, body lotions, cleansing lotions, eye cosmetics, shower oils, bath oils, deodorants, as well as in the form of decorative cosmetics such as makeup, lipstick, mascara, foundation, rouge, face tint, concealer, lip gloss, blush, eye-shadow.

In a transfer-proof lipstick it is possible to add up to 80% by weight of a mixture of silicone oils and high moleculare polydimethyl siloxanes, up to 30% by weight Alkanes or alkenes in hydrocarbons and up to 80% by weight water.

The manufacture of such products is carried out in a way known to a person skilled in the art. Decorative cosmetics are preferred, especially lipstick, makeup, mascara, foundation, eye-liner, rouge, concealer, eye-shadow or lip gloss.

In the following, the invention shall be described in detail by examples. All percent figures are by weight if not indicated otherwise.

Example 1

Lipstick I

Phase A

| | |
|---|---|
| Isododecane | 40 |
| Polybutene | 10 |
| Polyethylene | 10 |
| Preservatives | 1 |
| Colorants/Pigments | 10 |
| KF-880 (Shin-Etsu) | 1 |

Phase B

| | |
|---|---|
| Water | 28 |

The ingredients of phase A are heated to 95° C., mixed at 1500 RPM till uniform. Phase B is heated to 90-95° C. After that phase B is added to phase A and mixed till homogenous. Then the product is poured into lipstick moulds at 80° C.

Example 2

Lipstick II

To the ingredients of phase A of example 1 are added 1% Polyisobutene. The phase B water amount is reduced to 27%. The manufacturing process is the same as in example 1.

Example 3

Mascara I and II

Phase A

| | |
|---|---|
| Isododecane | 40 |
| Waxes | 10 |
| Colorants & Pigments | 10 |
| Preservatives | 1 |
| DC 2-8566 Amino Fluids | 2 |
| Abil ® Em-90 | 1 (I); 0.6 (II) |

Phase B

| | |
|---|---|
| Water | q.s. ad 100 |

Example 4

Lip Balm

Phase A

| | |
|---|---|
| Cetyl Dimethicone | 15 |
| Polybutene | 30 |
| Preservative | 1 |
| Dimethicone | 2 |
| DC 2-8566 ® Amino Fluids | 2 |

Phase B

| | |
|---|---|
| Water | q.s. ad 100 |

Example 5

Eye-Shadow I and II

Phase A

| | |
|---|---|
| Cetyl Dimethicone | 15 |
| Polybutene | 30 (I); 26 (II) |
| Preservative | 1 |
| Dimethicone | 2 |
| DC 2-8566 ® Amino Fluids | 1.8 (I); 0.5 (II) |

Phase B

| | |
|---|---|
| Water | q.s. ad 100 |

Example 6

Lipstick III

Phase A

| | |
|---|---|
| Isododecane | 40 |
| Polybutene | 8.5 |
| Polyethylene | 10 |
| Preservatives | 1 |
| Colorants/Pigments | 10 |
| KF-880 ® (Shin-Etsu) | 3.5 |

Phase B

| | |
|---|---|
| Water | q.s. ad 100 |

Example 7

Transferproof Lipstick

| | |
|---|---|
| Dimethiconol & Dimethicone | 20 |
| Cyclopentasiloxane & Dimethiconol | 30 |
| Polybutene/Isododecane (1:1) | 6 |
| Polyethylene wax (fluid) | 4 |
| KF-880 ® | 3 |
| Preservative | 0.3 |
| Colorants | 2 |
| Mica | 2 |
| Nylon beads | 2 |
| Water | qs. ad 100 |

Example 8

Longwaring Eyeshadow

| | |
|---|---|
| Dimethiconol & Dimethicone | 40 |
| Cyclopentasiloxane & Dimethiconol | 5 |
| Polybutene/Isododecane (1:1) | 6 |
| Polyethylene wax (fluid) | 1 |
| KF-880 ® | 2 |
| Preservative | 0.3 |
| Colorants | 1 |
| Mica | 2 |
| Nylon beads | 2 |
| Polyethylene wax (solid) | 5 |
| Water | qs. ad 100 |

Example 9

Face Tint

| | |
|---|---|
| Cyclopentasiloxane & Dimethiconol | 40 |
| Polybutene/Isododecane (1:1) | 5 |
| Polyethylene wax (fluid) | 1 |
| KF-880 ® | 3 |
| Preservative | 0.3 |
| Colorants | 1 |
| Mica | 1 |
| Nylon beads | 1 |
| Water | qs. ad 100 |

Example 10

Antiperspirant

| | |
|---|---|
| Cyclotetrasiloxane & Cyclohexasiloxane & Cyclopentasiloxane | 20 |
| PPG-3 Benzyl Ether Myristate | 2.5 |
| Glyceryl Isostearate & Caprylic/Capric Glycerides | 1.5 |
| Polyethylene | 7.0 |
| Ozokerite | 2.0 |
| Cetyl PEG/PPG-10/1 Dimethicone | 1.0 |
| Aminopropyl Dimethicone & Dimethicone | 1.5 |
| Water | qs. ad 100 |
| Aluminium zirconium tetrachlorohydrex GLY (36%) in water | 40 |
| Fragrance | 1 |

Examples 11 and 12

Comparative Examples

Stability tests were carried out in which 20 test objects in the form of sticks were stored in a climate-controlled room at a temperature of 50° C. and a relative air humidity of 55%. The test objects were composed according to Example 2 and according to Example 7.

Every two weeks, an inspection was carried out. After 8 weeks, no sweating was able to be observed in the sticks according to Example 2 nor in those according to Example 7. Neither could any bleeding be observed in any test object of the two types of sticks.

Example 13

Comparative Example

In tests carried out using test persons who were asked to evaluate the product with regard to 13 different aspects during the test phase, the overall evaluation of compositions according to Example 5 (I) was as follows (in % of the test persons):

| | |
|---|---|
| fair: | 12% |
| good: | 8% |
| very good: | 31% |
| excellent: | 47% |

The invention claimed is:

1. A cosmetic composition for skin care in the form of a cosmetic emulsion selected from the group consisting of O/W emulsions, W/O emulsions, and combinations thereof comprising 0.1 to 10% by weight of a single emulsifying agent,
   wherein the single emulsifying agent is amodimethicone, having 3-(2-aminoethyl)-aminopropyl groups and an amine equivalent of 1800 to 4500 g/mol,
   wherein the cosmetic composition excludes hair conditioning compositions and hair coloring compositions, and
   wherein the cosmetic composition does not comprise other emulsifying agents.

2. The cosmetic composition for skin care according to claim 1, wherein the amodimethicone has an amine equivalent of 1800 to 2200 g/mol.

3. The cosmetic composition for skin care according to claim 1, wherein the cosmetic emulsion is selected from the group consisting of an O/W emulsion and a W/O emulsion, wherein the cosmetic emulsion comprises a watery phase and an oily phase, wherein the watery phases comprises water, and wherein the oily phase comprises one selected from the group consisting of a monoester, a diester, a triester, a hydrocarbon, an alkane, an alkene, silicone oil, a mixture of silicone oils, a high viscosity polysiloxane, and combinations thereof.

4. The cosmetic composition for skin care according to claim 3, wherein the alkane is selected from the group consisting of isododecane, isohexadecane, and combinations thereof.

5. The cosmetic composition for skin care according to claim 1, wherein the emulsion comprises a polymeric component selected from the group consisting of polyethylene, polybutene, polyisobutene, polydecene, polyisoprene, ethylene/propylene/styrene copolymers, butylene/ethylene/styrene copolymers, combinations thereof, and copolymers thereof.

6. The cosmetic composition for skin care according to claim 1, wherein the cosmetic emulsion comprises Polybutene as film-forming agent.

7. The cosmetic composition for skin care according to claim 1, wherein the cosmetic emulsion comprises 0.4 to 7% by weight of the single emulsifying agent.

8. The cosmetic composition for skin care according to claim 7, wherein the cosmetic emulsion comprises 0.4 to 3.5% by weight of the single emulsifying agent.

9. The cosmetic composition for skin care according to claim 1, wherein the cosmetic emulsion comprises up to 80% by weight of a mixture of silicone oils and high molecular weight polydimethyl siloxanes.

10. The cosmetic composition for skin care according to claim 1, wherein the cosmetic emulsion is one selected from the group consisting of a sun screen cream, after sun product, day cream, night cream, face mask, body lotion, cleansing lotion, eye cosmetic, shower oil, bath oil, deodorant, lipstick, make-up, mascara, foundation, eye-liner, rouge, face tint, concealer, eyeshadow, lipgloss, and combinations thereof.

11. The cosmetic composition for skin care according to claim 1, wherein the cosmetic composition is a stick comprising water in an amount of from 40-55% by weight.

12. A method of emulsifying a cosmetic O/W emulsion, W/O emulsion, or multiple emulsions comprising adding to said cosmetic O/W emulsion, W/O emulsion, or multiple emulsion an emulsifying agent that is an amodimethicone which comprises 3-(2-aminoethyl)-aminopropyl groups and has an amine equivalent of 1800 to 4500 g/mol.

13. A method according to claim 12, wherein said cosmetic O/W emulsion, W/O emulsion, or multiple emulsion is electrolyte-free.

14. A method according to claim 12, wherein said cosmetic O/W emulsion, W/O emulsion, or multiple emulsion is anti-foam-free.

15. A method according to claim 12, comprising of 0.4 to 7% by weight of amodimethicone.

* * * * *